(12) United States Patent
Mizumoto et al.

(10) Patent No.: US 9,701,644 B2
(45) Date of Patent: Jul. 11, 2017

(54) SALT OF NITROGEN-CONTAINING HETEROCYCLIC COMPOUND OR CRYSTAL THEREOF, PHARMACEUTICAL COMPOSITION, AND FLT3 INHIBITOR

(71) Applicant: FUJIFILM Corporation, Tokyo (JP)

(72) Inventors: Shinsuke Mizumoto, Toyama (JP); Takuya Matsumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/130,168

(22) Filed: Apr. 15, 2016

(65) Prior Publication Data

US 2016/0229812 A1 Aug. 11, 2016

Related U.S. Application Data

(63) Continuation of application No. PCT/JP2014/077368, filed on Oct. 15, 2014.

(30) Foreign Application Priority Data

Oct. 16, 2013 (JP) .................. 2013-215755

(51) Int. Cl.
| | |
|---|---|
| C07D 239/42 | (2006.01) |
| A61K 31/505 | (2006.01) |
| C07D 239/48 | (2006.01) |
| C07C 55/10 | (2006.01) |
| C07C 57/15 | (2006.01) |
| C07C 65/11 | (2006.01) |
| C07C 309/29 | (2006.01) |

(52) U.S. Cl.
CPC .......... C07D 239/48 (2013.01); A61K 31/505 (2013.01); C07C 55/10 (2013.01); C07C 57/15 (2013.01); C07C 65/11 (2013.01); C07C 309/29 (2013.01); C07D 239/42 (2013.01); C07B 2200/13 (2013.01)

(58) Field of Classification Search
CPC ............................ C07D 239/42; A61K 31/505
USPC ................................... 544/323; 514/275
See application file for complete search history.

(56) References Cited

U.S. PATENT DOCUMENTS

| | | | |
|---|---|---|---|
| 8,703,767 B2 | 4/2014 | Bearss et al. | |
| 9,145,415 B2 * | 9/2015 | Takasaki | ............ C07D 403/12 |
| 2012/0035168 A1 | 2/2012 | Brandl et al. | |
| 2012/0149722 A1 | 6/2012 | Lee et al. | |
| 2013/0059847 A1 | 3/2013 | Bearss et al. | |
| 2015/0045339 A1 | 2/2015 | Takasaki et al. | |
| 2015/0225436 A1 | 8/2015 | Wang et al. | |

FOREIGN PATENT DOCUMENTS

| | | |
|---|---|---|
| CN | 102105150 A | 6/2011 |
| JP | 2009-515851 A | 4/2009 |
| WO | 91/09856 A1 | 7/1991 |
| WO | 2006/135713 A2 | 12/2006 |
| WO | 2007/054550 A1 | 5/2007 |
| WO | 2007/109120 A2 | 9/2007 |
| WO | 2009/095399 A2 | 8/2009 |
| WO | 2010/129053 A2 | 11/2010 |
| WO | 2012/061303 A1 | 5/2012 |
| WO | 2012/064706 A1 | 5/2012 |
| WO | 2012/135801 A1 | 10/2012 |
| WO | 2012/150952 A1 | 11/2012 |
| WO | 2013/157540 A1 | 10/2013 |
| WO | WO 2013/157540 | * 10/2013 |

OTHER PUBLICATIONS

Serajuddin, Advanced Drug Delivery Reviews 59 (2007) 603-616.*
Bastin et al., Organic Process Research & Development 2000, 4, 427-435.*
Liu, Rong, ed., Water-Insoluble Drug Formulation (CRC Press, 2008) Chapter 15 pp. 417-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Swarbrick et al., eds. Encyclopedia of Pharmaceutical Technology 13 (Marcel Dekker, NY 1996) pp. 453-499.*
Gould, International J. of Therapeutics 33,201 (1986).*
Extended European Search Report dated Aug. 9, 2016 from the European Patent Office in counterpart European Application No. 14854750.8.
P. Brown et al., "FLT3 Inhibitors: a paradigm for the development of targeted therapeutics for paediatric cancer", European Journal of Cancer, 2004, pp. 707-721, vol. 40.

(Continued)

Primary Examiner — Deepak Rao
(74) Attorney, Agent, or Firm — Sughrue Mion, PLLC

(57) ABSTRACT

An object of the present invention is to provide a compound and pharmaceutical composition showing superior stability and/or solubility, etc. and having superior FLT3 inhibitory activity. The present invention provides a salt of (S,E)-N-(1-((5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-enamide, or a crystal thereof. Since the salt or a crystal thereof has superior FLT3 inhibitory activity and shows superior physicochemical properties as drugs, such as storage stability, solubility, and so forth, it is useful for treatments of diseases or conditions relating to FLT3. The present invention also provides a pharmaceutical composition and FLT3 inhibitor containing the salt or a crystal thereof.

(Compound A)

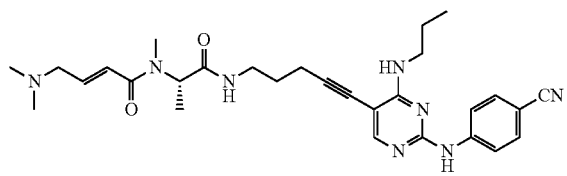

2 Claims, 3 Drawing Sheets

(56) References Cited

OTHER PUBLICATIONS

"Cancer Facts and Figures", American Cancer Society, 2012, pp. 9-24.

S. Yokota et al., "Internal tandem duplication of the Flt3 gene is preferentially seen in acute myeloid leukemia and myelodysplastic syndrome among various hematological malignancies. A study on a large series of patients and cell lines", Leukemia, 1997, pp. 1605-1609, vol. 11.

Chunaram Choudhary et al., "AML-associated Flt3 kinase domain mutations show signal transduction differences compared with Flt3 ITD mutations", Blood, Jul. 1, 2005, pp. 265-273, vol. 106, No. 1.

Hitoshi Kiyoi et al., "Mechanism of constitutive activation of FLT3 with internal tandem duplication in the juxtamembrane domain", Oncogene, 2002, pp. 2555-2563, vol. 21.

International Search Report for PCT/JP2014/077368 dated Dec. 22, 2014.

Written Opinion for PCT/JP2014/077368 dated Dec. 22, 2014.

International Search Report for PCT/JP2013/061273 dated Jun. 4, 2013.

Written Opinion for PCT/JP2013/061273 dated Jun. 4, 2013.

International Preliminary Report on Patentability for PCT/JP2013/061273 dated Oct. 21, 2014.

Extended European Search Report issued in European Patent Application No. 13778349.4 on Aug. 26, 2015.

Chinese Office Action issued in Chinese Patent Application No. 201380020639.X on Jul. 3, 2015.

deVries et al., 92 Haematologica, 1557-1560 (2007).

D. Gilliland et al., 100 Blood 1532-1542 (2002).

CAS Registry Nos. 1208542-16-8; 1211912-67-2 (2010).

J.H. Poupaert, Drug Design: Basic Principles and Applications, in 2 Encyclopedia of Pharmaceutical Technology 1362-1369, 1367 (James Swarbrick ed., 3rd ed., 2007).

B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).

J. Cools et al., 64 Cancer Research, 6385-6389 (2004).

K.W. Pratz et al., 115 Blood, 1425-1432 (2010).

CAS Registry No. 1370823-68-9 (2012).

International Preliminary Report on Patentability dated Apr. 28, 2016 from the International Bureau in counterpart International Application No. PCT/JP2014/077368.

Office Action dated Mar. 22, 2017, from the State Intellectual Property Office of People's Republic of China in counterpart Chinese Application No. 201480056478.4.

\* cited by examiner

SALT OF NITROGEN-CONTAINING HETEROCYCLIC COMPOUND OR CRYSTAL THEREOF, PHARMACEUTICAL COMPOSITION, AND FLT3 INHIBITOR

CROSS REFERENCE OF THE RELATED APPLICATION

This application is a Continuation of PCT International Application No. PCT/JP2014/077368 filed on Oct. 15, 2014, which claims priority under 35 U.S.C §119(a) to Japanese Patent Application No. 2013-215755 filed on Oct. 16, 2013. Each of the above application(s) is hereby expressly incorporated by reference, in its entirety, into the present application.

TECHNICAL FIELD

The present invention relates to a salt of a nitrogen-containing heterocyclic compound or a crystal thereof, which is useful as an Fms-like tyrosine kinase 3 inhibitor.

BACKGROUND ART

The Fms-like tyrosine kinase 3 (FLT3) is a protein belonging to the class III of receptor type tyrosine kinases, and it has five immunoglobulin-like motifs in the N-terminus extracellular domain, and two kinase domains at the C-terminus. Expression of FLT3 is observed on normal CD34-positive human bone marrow precursor cells and dendritic cells, and it plays an important role for proliferation, differentiation, and so forth of these cells (Non-patent document 1). Further, the ligand (FL) of FLT3 is expressed in bone marrow stromal cells and T cells, and is one of the cytokines that affect the cytogenesis of many kinds of hematogenous systems, and stimulate proliferation of stem cells, precursor cells, dendritic cells, and natural killer cells through interactions with other growth factors.

FLT3 is dimerized upon binding of FL, and activated by autophosphorylation. As a result, phosphorylation of PI3 as well as AKT and ERK in the RAS signal transduction pathway is induced. FLT3 plays an important role for proliferation and differentiation of hematopoietic cells.

In normal bone marrow, expression of FLT3 is limited to early precursor cells, but in blood carcinoma, FLT3 is overexpressed, or FLT3 causes a mutation, and thereby contributes to proliferation and malignant alteration of carcinoma through activation of the aforementioned signal transduction pathway. The blood carcinoma include, for example, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell leukemia (ATL), myelodysplastic syndrome (MDS), and myeloproliferative disorder (MPD).

As for AML among the blood carcinomas, several existing therapies are effective to a certain extent, but relapse and resistance are frequently observed, and it is still such an intractable carcinoma as the five-year survival rate for that carcinoma is about 24% (in the United States) (Non-patent document 2). One of the causes of the relapse and resistance thereof is gene mutation of the AML cells, and especially, gene mutation of FLT3 is confirmed most frequently. It is known that the FLT3 gene mutation includes internal tandem duplication (ITD) mutation observed near the membrane (Non-patent document 3) and activation mutation of the tyrosine kinase site (Non-patent document 4), and FLT3 is constantly activated even in the absence of the ligand to accelerate proliferation of cancer cells.

It is reported that the ITD mutation, in particular, is observed in about 30% of AML patients, and vital prognosis of the patients having this mutation is poor (Non-patent document 5).

It is thought that suppression of both the activation of FLT3 and the activation thereof by gene mutation is important for the treatment of AML and improvement of prognosis, and development of FLT3 inhibitor is conducted.

For example, AC220 (Ambit) is a compound that selectively inhibits type III tyrosine kinases (FLT3, c-KIT, FMS, PDGFR), and it is developed with targeting AML (Patent document 1).

Further, drugs showing superior activity and sustainability by covalently bonding to a biological protein have been developed and marketed. For example, Afatinib (BIBW2992) has been reported as an EGFR inhibitor having acrylic group in the molecule (Patent document 2), and marketed in the United States.

PRIOR ART REFERENCES

Patent Documents

Patent document 1: WO2007/109120A2
Patent document 2: Japanese Patent Unexamined Publication (Kohyo) No. 2009-515851

Non-Patent Documents

Non-patent document 1: Brown P. et al., European Journal of Cancer, vol. 40, pp. 707-721, 2004
Non-patent document 2: American Cancer Society, Cancer Facts and Figures, pp. 9-24, 2012
Non-patent document 3: Yokota S. et al., Leukemia, vol. 11, pp. 1605-1609, 1997
Non-patent document 4: Choudhary C. et al., Blood, vol. 106, pp. 265-273, 2005
Non-patent document 5: Kiyoi H. et al., Oncogene, vol. 21, pp. 2555-2563, 2002

SUMMARY OF THE INVENTION

Object to be Achieved by the Invention

Conventional FLT3 inhibitors do not necessarily have sufficient FLT3 inhibitory action, and compound and pharmaceutical composition showing higher FLT3 inhibitory activity are desired. Further, there are desired compound and pharmaceutical composition having an FLT3 inhibitory action, which show superior storage stability and/or solubility etc. and thus are useful as an active ingredient of drugs.

Means for Achieving the Object

The inventors of the present invention conducted various researches under such a situation as described above. As a result, they found that a salt of (S,E)-N-(1-((5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-enamide (henceforth also referred to as compound A) or a crystal thereof has superior FLT3 inhibitory activity, storage stability and/or solubility, and so forth, and thus is useful as an active ingredient of drugs, and accomplished the present invention on the basis of these findings.

The present invention thus provides the followings.

[1] A carboxylic acid salt (carboxylate), a mineral acid salt, or a sulfonic acid salt (sulfonate) of the compound A.

[2] The salt according to [1], which is a carboxylate.

[3] The salt according to [1], which is a mineral acid salt.

[4] The salt according to [2], wherein the carboxylate is formate, acetate, lactate, benzoate, citrate, oxalate, fumarate, maleate, succinate, malate, tartrate, aspartate, trichloroacetate, trifluoroacetate, or pamoate.

[5] The salt according to [2], wherein the carboxylate is fumarate, succinate, or pamoate.

[6] The salt according to [3], wherein the mineral acid salt is hydrochloride, hydrobromide, hydroiodide, nitrate, phosphate, or sulfate.

[7] The salt according to [3], wherein the mineral acid salt is hydrochloride or hydrobromide.

[8] A crystal of succinate of the compound A, which shows diffraction peaks at diffraction angles (2θ) of 10.5, 17.1, 19.1, and 22.4° in powder X-ray diffractometry.

[9] A crystal of succinate of the compound A, which shows diffraction peaks at diffraction angles (2θ) of 12.8, 16.1, 21.4, and 28.00 in powder X-ray diffractometry.

[10] A crystal of fumarate of the compound A, which shows diffraction peaks at diffraction angles (2θ) of 8.6, 13.7, 17.8, and 23.0° in powder X-ray diffractometry.

[11] A pharmaceutical composition containing the salt according to any one of [1] to [7], or the crystal according to any one of [8] to [10].

[12] An FLT3 inhibitor containing the salt according to any one of [1] to [7], or the crystal according to any one of [8] to [10].

The present invention further provides the followings.

(a) A salt of the compound A or a crystal thereof for use as a drug.

(b) A salt of the compound A or a crystal thereof for use in a treatment of a disease or condition relating to FLT3, preferably for use in a treatment of ALL, AML, APL, CLL, CML, CNL, AUL, ALCL, PML, JMML, ATL, MDS or MPD, more preferably for use in a treatment of AML or APL, still more preferably for use in a treatment of AML.

(c) A pharmaceutical composition containing a salt of the compound A or a crystal thereof and a pharmaceutically acceptable additive.

(d) Use of a salt of the compound A or a crystal thereof for manufacture of a drug for use in a treatment of a disease or condition relating to FLT3, preferably for use in a treatment of ALL, AML, APL, CLL, CML, CNL, AUL, ALCL, PML, JMML, ATL, MDS or MPD, more preferably for use in a treatment of AML or APL, still more preferably for use in a treatment of AML.

(e) A method for a treatment of a disease relating to FLT3, preferably for use in a treatment of ALL, AML, APL, CLL, CML, CNL, AUL, ALCL, PML, JMML, ATL, MDS or MPD, more preferably for use in a treatment of AML or APL, still more preferably for use in a treatment of AML, which comprises the step of administrating a therapeutically effective amount of a salt of the compound A or a crystal thereof to an object (mammal including human) in need of such a treatment.

(f) A method for producing the salt according to any one of [1] to [7], or the crystal according to any one of or [8] to [10], which comprises the step of converting the compound A into a pharmaceutically acceptable salt thereof.

Effect of the Invention

According to the present invention, there can be provided a salt of a nitrogen-containing heterocyclic compound or a crystal thereof showing superior FLT3 inhibitory action, storage stability and/or solubility etc. and thus useful as an active ingredient of drugs.

MODES FOR CARRYING OUT THE INVENTION

Figure 1:
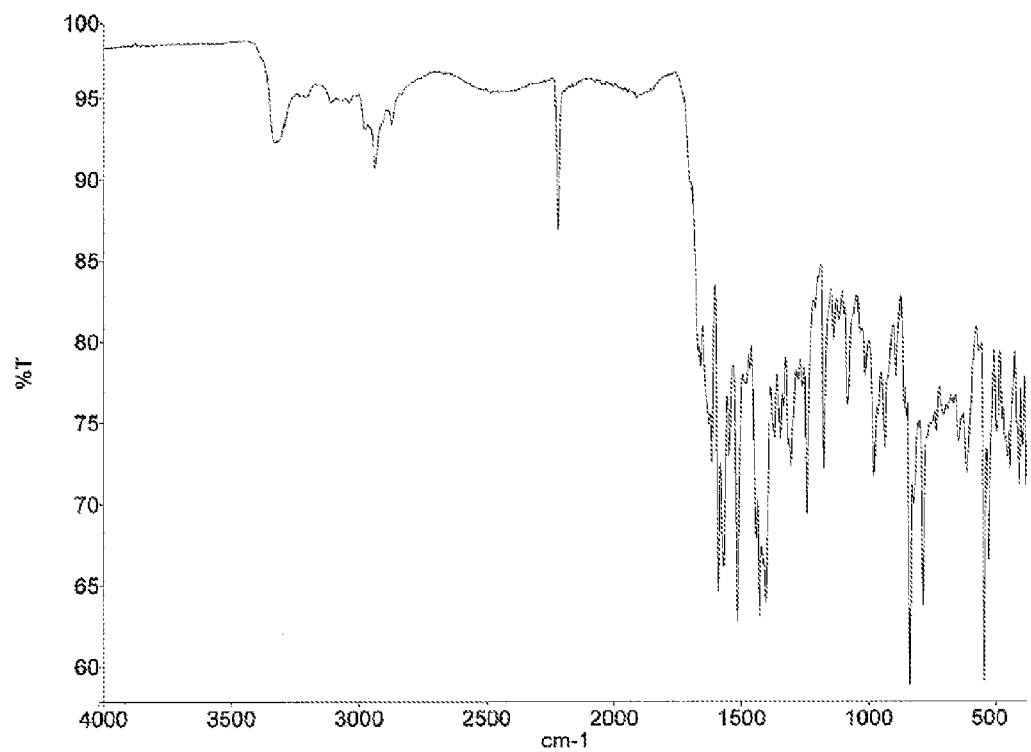
FIG. 1 shows an example of infrared absorption spectrum (ATR method) of α-form crystal of succinate of the compound A.

Hereafter, the present invention will be explained in detail.

In the present invention, the numerical value ranges shown with "to" means ranges including the numerical values indicated before and after "to" as the minimum and maximum values, respectively. In the present invention, when two or more kinds of substances corresponding an ingredient of a composition are present in the composition, the amount of the ingredient means the total amount of two or more kinds of the substances present in the composition, unless especially indicated.

In the present invention, the terms have the following meanings unless especially specified.

A halogen atom means fluorine atom, chlorine atom, bromine atom, or iodine atom.

A $C_{1-6}$ alkyl group means a linear or branched $C_{1-6}$ alkyl group such as methyl, ethyl, propyl, isopropyl, butyl, sec-butyl, isobutyl, tert-butyl, pentyl, isopentyl, 2-methylbutyl, 2-pentyl, 3-pentyl, and hexyl groups.

An ar($C_{1-6}$ alkyl) group means an ar($C_{1-6}$ alkyl) group such as benzyl, diphenylmethyl, trityl, phenethyl, 2-phenylpropyl, 3-phenylpropyl, and naphthylmethyl groups.

A $C_{1-6}$ alkoxy group means a linear, branched, or cyclic $C_{1-6}$ alkyloxy group such as methoxy, ethoxy, propoxy, isopropoxy, cyclopropoxy, butoxy, isobutoxy, sec-butoxy, tert-butoxy, cyclobutoxy, pentyloxy, and hexyloxy groups.

A ($C_{1-6}$ alkoxy)($C_{1-6}$ alkyl) group means a ($C_{1-6}$ alkyloxy)($C_{1-6}$ alkyl) group such as methoxymethyl and 1-ethoxyethyl groups.

A $C_{2-6}$ alkanoyl group means a linear or branched $C_{2-6}$ alkanoyl group such as acetyl, propionyl, valeryl, isovaleryl, and pivaloyl groups.

An aroyl group means benzoyl or naphthoyl group.

A heterocyclylcarbonyl group means furoyl, thenoyl, pyrrolidinylcarbonyl, piperidinylcarbonyl, piperazinylcarbonyl, morpholinylcarbonyl, or pyridinylcarbonyl group.

An acyl group means formyl group, succinyl group, glutaryl group, maleoyl group, phthaloyl group, a $C_{2-6}$ alkanoyl group, aroyl group, or a heterocyclylcarbonyl group.

A C$_{1-6}$alkoxycarbonyl group means a linear or branched C$_{1-6}$ alkyloxycarbonyl group such as methoxycarbonyl, ethoxycarbonyl, isopropoxycarbonyl, tert-butoxycarbonyl, and 1,1-dimethylpropoxycarbonyl groups.

An ar(C$_{1-6}$ alkoxy)carbonyl group means an ar(C$_{1-6}$ alkyloxy)carbonyl group such as benzyloxycarbonyl and phenethyloxycarbonyl groups.

An aryloxycarbonyl group means phenyloxycarbonyl or naphthyloxycarbonyl group.

A C$_{1-6}$ alkylsulfonyl group means a C$_{1-6}$ alkylsulfonyl group such as methylsulfonyl, ethylsulfonyl, and propylsulfonyl groups.

An arylsulfonyl group means benzenesulphonyl, p-toluenesulfonyl, or naphthalenesulfonyl group.

A C$_{1-6}$ alkylsulfonyloxy group means a C$_{1-6}$ alkylsulfonyloxy group such as methylsulfonyloxy and ethylsulfonyloxy groups.

An arylsulfonyloxy group means benzenesulfonyloxy or p-toluenesulfonyloxy group.

A silyl group means trimethylsilyl, triethylsilyl, or tributylsilyl group.

A leaving group means a halogen atom, a C$_{1-6}$ alkylsulfonyloxy group, or an arylsulfonyloxy group. The C$_{1-6}$ alkylsulfonyloxy group, and arylsulfonyloxy group may be substituted with one or more groups selected from a halogen atom, nitro group, a C$_{1-6}$ alkyl group, and a C$_{1-6}$ alkoxy group.

The amino-protecting group may be any group that can be used as a usual protective group of amino group. Examples include, for example, the groups mentioned in T. W. Greene et al., Protective Groups in Organic Synthesis, 4th Edition, pp. 696-926, 2007, John Wiley & Sons, Inc. Specific examples include an ar(C$_{1-6}$ alkyl) group, a (C$_{1-6}$ alkoxy) (C$_{1-6}$ alkyl) group, an acyl group, a C$_{1-6}$ alkoxycarbonyl group, an ar(C$_{1-6}$ alkoxy)carbonyl group, an aryloxycarbonyl group, a C$_{1-6}$ alkylsulfonyl group, an arylsulfonyl group, and a silyl group.

An aliphatic hydrocarbons mean pentane, hexane, heptane, cyclohexane, methylcyclohexane, or ethylcyclohexane.

A halogenated hydrocarbon means dichloromethane, chloroform, or dichloroethane.

An ether means diethyl ether, diisopropyl ether, tetrahydrofuran, 2-methyltetrahydrofuran, 1,4-dioxane, anisole, ethylene glycol dimethyl ether, diethylene glycol dimethyl ether, or diethylene glycol diethyl ether.

An alcohol means methanol, ethanol, propanol, 2-propanol, butanol, 2-methyl-2-propanol, ethylene glycol, propylene glycol, or diethylene glycol.

A ketone means acetone, 2-butanone, 4-methyl-2-pentanone, or methyl isobutyl ketone.

An ester means methyl acetate, ethyl acetate, propyl acetate, isopropyl acetate, or butyl acetate.

An amide means N,N-dimethylformamide, N,N-dimethylacetamide, or N-methylpyrrolidone.

A nitrile means acetonitrile or propionitrile.

A sulfoxide means dimethyl sulfoxide or sulfolane.

An aromatic hydrocarbon means benzene, toluene, or xylene.

An inorganic base means sodium hydroxide, potassium hydroxide, sodium methoxide, tert-butoxysodium, tert-butoxypotassium, sodium hydrogencarbonate, sodium carbonate, potassium carbonate, tripotassium phosphate, potassium acetate, cesium fluoride, or cesium carbonate.

An organic base means triethylamine, N,N-diisopropylethylamine, 1,8-diazabicyclo(5.4.0)undec-7-ene (DBU), pyridine, 4-dimethylaminopyridine, or N-methylmorpholine.

A prophylactic treatment means a treatment for inhibiting onset, reducing risk of onset, retarding onset, etc.

A therapeutic treatment means a treatment for improving a target disease or condition, or suppressing (maintaining or retarding) aggravation of the disease or condition.

A treatment means a prophylactic treatment, therapeutic treatment, or the like for any of various diseases.

Hereafter, the methods for preparing the compound of the present invention will be explained.

A salt of the compound A is prepared by a combination of per se known methods, and for example, it can be prepared by the preparation methods shown below.

Preparation Method 1

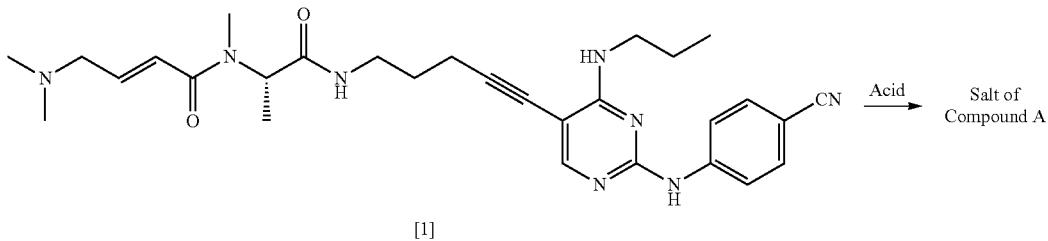

[Formula 1]

[1]

A salt of the compound A can be produced by suspending the compound A (compound of the formula [1]) in a solvent, adding an acid to the suspension, heating the mixture to dissolve the compound, and then cooling the solution.

Examples of the solvent used for this reaction include, for example, ethers, alcohols, ketones, esters, nitriles, sulfoxides, aromatic hydrocarbons, and water, and these may be used as a mixture of two or more kinds of them.

Preferred examples of the solvent include tetrahydrofuran, 2-methyltetrahydrofuran, 1,4-dioxane, methanol, ethanol, 2-propanol, 1-butanol, 2-buthanol, acetone, 2-butanone, methyl isobutyl ketone, ethyl acetate, isopropyl acetate, acetonitrile, dimethyl sulfoxide, toluene, and water, and 1,4-dioxane, ethanol, acetone, acetonitrile, and water are more preferred.

Volume of the solvent to be used with respect to the compound A may be 2- to 120-fold volume (v/w), preferably 4- to 60-fold volume (v/w), more preferably 5- to 30-fold volume (v/w).

Examples of the acid used for this reaction include carboxylic acid, mineral acid, and sulfonic acid.

Examples of the carboxylic acid include formic acid, acetic acid, lactic acid, benzoic acid, citric acid, oxalic acid, fumaric acid, maleic acid, succinic acid, malic acid, tartaric acid, aspartic acid, trichloroacetic acid, trifluoroacetic acid, and pamoic acid. Acetic acid, lactic acid, benzoic acid, citric acid, oxalic acid, fumaric acid, maleic acid, succinic acid, malic acid, tartaric acid, and pamoic acid are preferred, fumaric acid, succinic acid, and pamoic acid are more preferred, fumaric acid and succinic acid are still more preferred, and succinic acid is most preferred.

Examples of the mineral acid include hydrochloric acid, hydrobromic acid, hydroiodic acid, nitric acid, phosphoric acid, and sulfuric acid. Hydrochloric acid, hydrobromic acid, nitric acid, phosphoric acid, and sulfuric acid are preferred, and hydrochloric acid and hydrobromic acid are more preferred.

Examples of the sulfonic acid include methanesulfonic acid, benzenesulfonic acid, p-toluenesulfonic acid, mesitylenesulfonic acid, and naphthalenesulfonic acid, and benzenesulfonic acid is preferred.

Amount of the acid to be used may be, although it depends on the type of the acid, 0.5 to 4.0 equivalents, preferably 1.0 to 2.0 equivalents, more preferably 1.0 to 1.5 equivalents, with respect to the compound A.

Preparation Method 2

A salt of the compound A can be prepared by suspending the compound A in a solvent 1, adding an acid to the suspension, heating the mixture to dissolve the compound, then cooling the mixture, and subsequently adding a solvent 2.

Type and amount of the solvent 1 used for this reaction are the same as those described for the preparation method 1.

Type and amount of the acid used for this reaction are the same as those described for the preparation method 1.

Examples of the solvent 2 used for this reaction include, for example, aliphatic hydrocarbons, halogenated hydrocarbons, ethers, alcohols, ketones, esters, nitriles, and aromatic hydrocarbons, and these may be used as a mixture of two or more kinds of them.

Preferred examples of the solvent 2 include tetrahydrofuran, ethanol, 2-propanol, acetone, methyl ethyl ketone, ethyl acetate, isopropyl acetate, acetonitrile, and toluene.

Volume of the solvent 2 to be used with respect to the compound A may be 2- to 120-fold volume (v/w), preferably 4- to 60-fold volume (v/w), more preferably 5- to 30-fold volume (v/w).

A salt of the compound A obtained by the aforementioned preparation methods can be purified by usual methods such as recrystallization.

Hereafter, the preparation methods of the compound A used for the preparation of the compound of the present invention will be explained.

The compound A can be produced by, for example, the following preparation method.

Preparation Method A

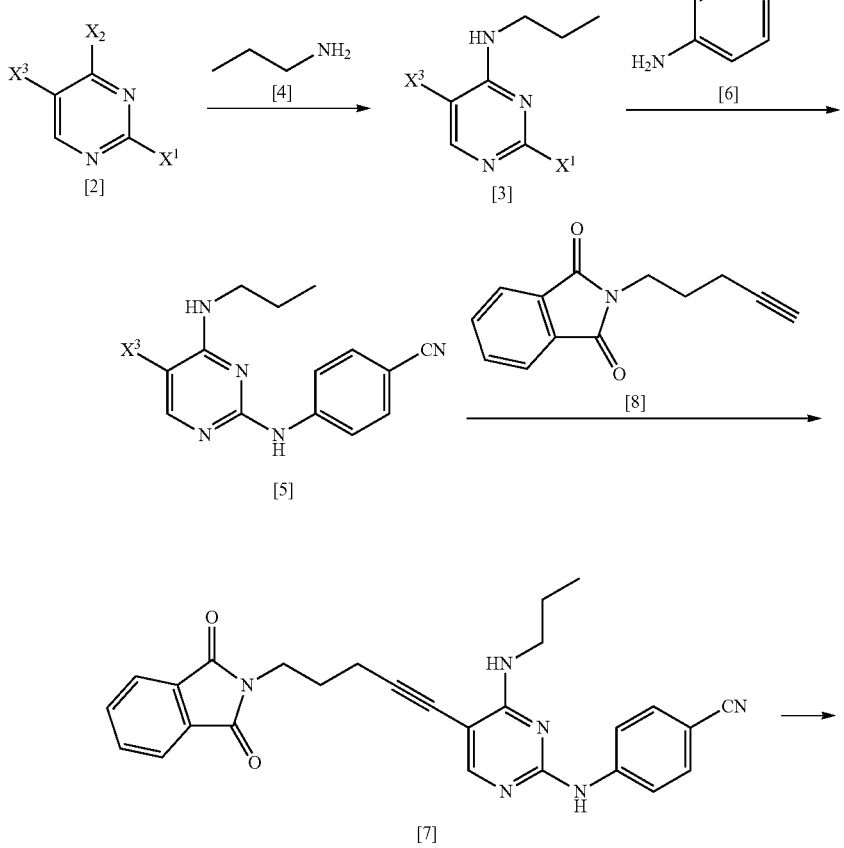

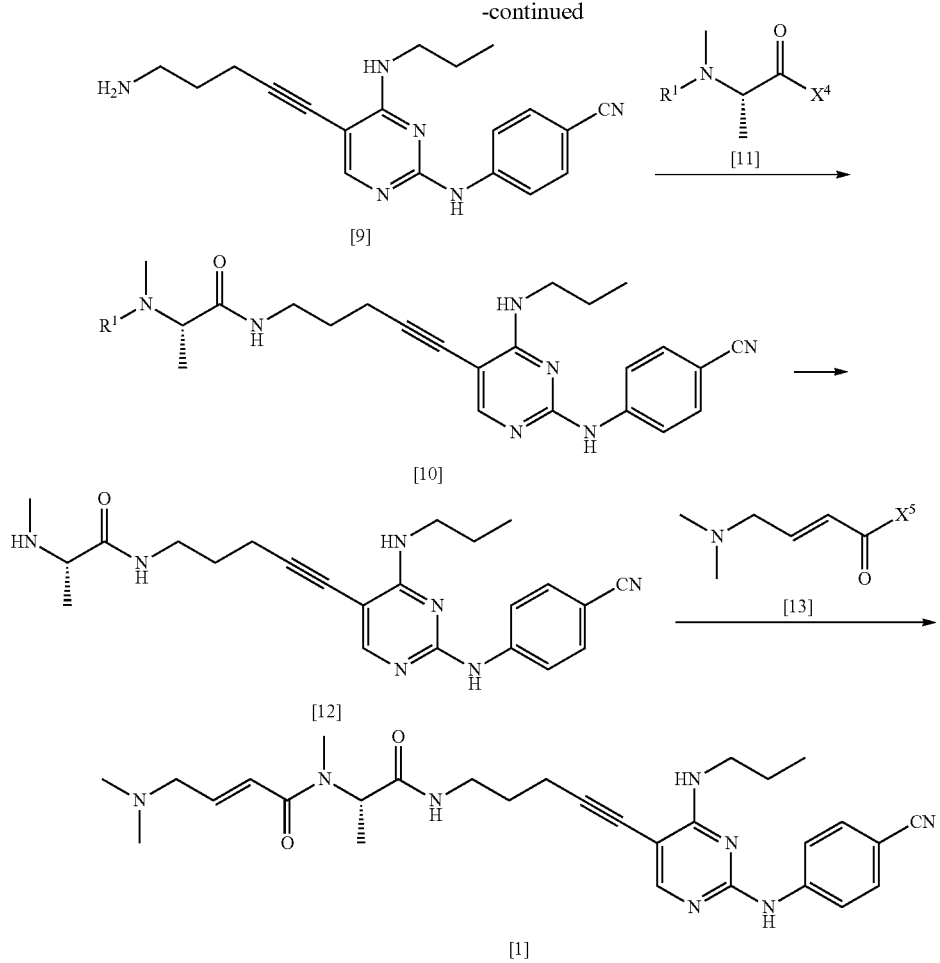

In the formula, $R^1$ represents an amino-protecting group; $X^1$, $X^2$, and $X^3$ are the same or different, and represent a leaving group; $X^4$ and $X^5$ are the same or different, and represent hydroxyl group or a leaving group.

(1)

As the compound of the general formula [2], for example, 2,4-dichloro-5-iodopyrimidine is known.

The compounds of the general formula [3] or a salt thereof can be prepared by reacting a compound of the general formula [2] with the compound of the formula [4] or a salt thereof in the presence of a base.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and these solvents may be used as a mixture of two or more kinds of them.

Preferred examples of the solvent include ethers, and tetrahydrofuran is more preferred.

Although volume of the solvent to be used is not particularly limited, it may be 1- to 500-fold volume (v/w) with respect to the compound of the general formula [2].

Amount of the compound of the formula [4] to be used may be 1- to 50-fold molar amount, preferably 1- to 5-fold molar amount, with respect to the compound of the general formula [2].

Examples of the base used for this reaction include inorganic bases and organic bases.

Preferred examples of the base include organic bases. Triethylamine and diisopropylethylamine are more preferred, and diisopropylethylamine is further preferred.

Amount of the base to be used may be 1- to 50-fold molar amount, preferably 1- to 5-fold molar amount, with respect to the compound of the general formula [2].

This reaction can be performed at −30 to 150° C., preferably 0 to 100° C., for 30 minutes to 48 hours.

(2)

The compounds of the general formula [5] can be prepared by reacting a compound of the general formula [3] with the compound of the formula [6].

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and these solvents may be used as a mixture of two or more kinds of them.

Preferred examples of the solvent include amides, and N-methylpyrrolidone is more preferred.

Although volume of the solvent to be used is not particularly limited, it may be 1- to 500-fold volume (v/w) with respect to the compound of the general formula [3].

Amount of the compound of the formula [6] to be used may be 1- to 50-fold molar amount, preferably 1- to 10-fold molar amount, with respect to the compound of the general formula [3].

It is preferable to use a proton acid for this reaction.

Examples of the proton acid include sulfonic acids and mineral acids. Methanesulfonic acid, camphorsulfonic acid, and hydrochloric acid are preferred, and camphorsulfonic acid is more preferred.

Amount of the proton acid to be used may be 1- to 50-fold molar amount, preferably 1- to 10-fold molar amount, with respect to the compound of the general formula [3].

This reaction can be performed at −30 to 150° C., preferably 0 to 100° C., for 30 minutes to 48 hours.

(3)

The compound of the formula [7] can be prepared by reacting a compound of the general formula [5] with the compound of the formula [8] in the presence of a palladium catalyst, a copper salt, and a base.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and these solvents may be used as a mixture of two or more kinds of them.

Preferred examples of the solvent include amides, and N,N-dimethylformamide is more preferred.

Although volume of the solvent to be used is not particularly limited, it may be 1- to 500-fold volume (v/w) with respect to the compound of the general formula [5].

Amount of the compound of the formula [8] to be used may be 1- to 50-fold molar amount, preferably 1- to 5-fold molar amount, with respect to the compound of the general formula [5].

Examples of the palladium catalyst used for this reaction include metal palladium such as palladium/carbon and palladium black; inorganic palladium salts such as palladium chloride; organic palladium salts such as palladium acetate; organic palladium complexes such as chloro(2-(dicyclohexylphosphino)-3,6-dimethoxy-2',4',6'-triisopropyl-1,1'-biphenyl)(2-(2-aminoethyl)phenyl)palladium(II), tetrakis(triphenylphosphine)palladium(0), bis(triphenylphosphine)palladium(II) dichloride, bis(di-tert-butyl(4-dimethylaminophenyl)phosphine)dichloropalladium(II), 1,1'-bis-(diphenylphosphino)ferrocenepalladium(II) dichloride, (E)-di(μ-acetato)bis(o-(di-o-tolylphosphino)benzyl)dipalladium (II), and tris(dibenzylidene acetone)dipalladium (0); polymer-supported organic palladium complexes such as polymer-supported bis(acetato)triphenylphosphinepalladium(II) and polymer-supported di(acetato)dicyclohexylphenylphosphinepalladium(II), and so forth, and organic palladium complexes are preferred.

Amount of the palladium catalyst to be used may be 0.0001- to 2-fold molar amount, preferably 0.001- to 0.2-fold molar amount, with respect to the compound of the general formula [5].

Examples of the copper salt used for this reaction include copper(I) chloride, copper(I) bromide, copper(I) iodide, and copper(II) acetate, and copper(I) iodide is preferred.

Amount of the copper salt to be used may be 0.0001- to 2-fold molar amount, preferably 0.001- to 0.5-fold molar amount, with respect to the compound of the general formula [5].

Examples of the base used for this reaction include organic bases. Triethylamine and diisopropylethylamine are preferred, and triethylamine is more preferred.

Amount of the base to be used may be 0.1- to 50-fold molar amount, preferably 1- to 10-fold molar amount, with respect to the compound of the general formula [5].

This reaction may be performed at −30 to 150° C., preferably 0 to 100° C., for 30 minutes to 48 hours.

(4)

The compound of the formula [9] can be prepared by carrying out deprotection of the compound of the formula [7].

This reaction can be performed by the method described in T. W. Greene et al., Protective Groups in Organic Synthesis, 4th edition, pp. 790-793, 2007, John Wiley & Sons, Inc.

(5)

(5-A) When $X^4$ is hydroxyl group:

As the compounds of the general formula [11], for example, N-(tert-butoxycarbonyl)-N-methyl-L-alanine is known.

The compounds of the general formula [10] can be prepared by reacting the compound of the formula [9] with a compound of the general formula [11] in the presence of a condensing agent or an acid halide.

This reaction can be performed by, for example, the method described in Chemical Reviews, vol. 97, p. 2243, 1997, Chemical Synthesis of Natural Product Peptides: Coupling Methods for the Incorporation of Noncoded Amino Acids into Peptides, or Tetrahedron, vol. 60, p. 2447, 2004, Recent development of peptide coupling reagents in organic synthesis.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and these solvents may be used as a mixture of two or more kinds of them.

Preferred examples of the solvent include amides, and N,N-dimethylformamide is more preferred.

Although volume of the solvent to be used is not particularly limited, it may be 1- to 500-fold volume (v/w) with respect to the compound of the formula [9].

Examples of the base used for this reaction include inorganic bases and organic bases.

Preferred examples of the base include organic bases. Triethylamine and diisopropylethylamine are preferred, and diisopropylethylamine is more preferred.

Amount of the base to be used may be 1- to 50-fold molar amount, preferably 1- to 10-fold molar amount, with respect to the compound of the formula [9].

Examples of the condensing agent used for this reaction include, for example, carbodiimides such as N,N'-dicyclohexylcarbodiimide and 1-ethyl-3-(3-dimethylaminopropyl)carbodiimide; carbonyl compounds such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium hexafluorophosphate; O-(7-azabenzotriazol-1-yl)-1,1,3,3-tetramethyluronium hexafluorophosphate, and so forth. Carbodiimides are preferred, and 1-ethyl-3-(3-dimethylaminopropyl)carbodiimide is more preferred.

When a carbodiimide is used as the condensing agent, it is preferable to use an additive.

Examples of the additive include N-hydroxysuccinimide, 1-hydroxybenzotriazole, and 1-hydroxy-7-azabenzotriazole, and 1-hydroxybenzotriazole is preferred.

Amount of the additive to be used may be 0.01- to 10-fold molar amount, preferably 0.1- to 1-fold molar amount, with respect to the compound of the formula [9].

Examples of the acid halide used for this reaction include, for example, carboxylic acid halides such as acetyl chloride and trifluoroacetyl chloride; sulfonic acid halides such as methanesulfonyl chloride and para-toluenesulfonyl chloride; and chloroformic acid esters such as ethyl chloroformate and isobutyl chloroformate.

Amount of the compound of the general formula [11] to be used is not particularly limited, and it may be 1- to 10-fold molar amount with respect to the compound of the formula [9].

This reaction may be performed at −30 to 150° C., preferably 0 to 100° C., for 30 minutes to 48 hours.

(5-B) When $X^4$ is leaving group:

The compounds of the general formula [10] can be prepared by reacting the compound of the formula [9] with a compound of the general formula [11] in the presence of a base.

The solvent used for this reaction is not particularly limited, so long as a solvent that does not affect the reaction is chosen, and examples include, for example, halogenated hydrocarbons, ethers, esters, amides, nitriles, and aromatic hydrocarbons, and these solvents may be used as a mixture of two or more kinds of them.

Although volume of the solvent to be used is not particularly limited, it may be 1- to 500-fold volume (v/w) with respect to the compound of the formula [9].

Examples of the base used for this reaction include inorganic bases and organic bases.

Amount of the base to be used may be 1- to 50-fold molar amount, preferably 1- to 5-fold molar amount, with respect to the compound of the formula [9].

Although amount of the compound of the general formula [11] to be used is not particularly limited, it may be 1- to 10-fold molar amount with respect to the compound of the formula [9].

This reaction may be performed at −30 to 150° C., preferably 0 to 100° C., for 30 minutes to 48 hours.

(6)

The compound of the formula [12] can be prepared by carrying out deprotection of the compound of the general formula [10].

This reaction can be performed by, for example, the method described in T. W. Greene et al., Protective Groups in Organic Synthesis, 4th Edition, pp. 696-926, 2007, John Wiley & Sons, Inc.

(7)

The compound of the formula [1] can be prepared by reacting the compound of the formula [12] with a compound of the general formula [13] in the presence of a condensing agent or an acid halide.

This reaction can be performed in a manner similar to that of [Preparation method A], (5).

When there are solvates, hydrates and crystals of various forms of the compounds used in the aforementioned preparation methods, these solvates, hydrates and crystals of various forms can also be used.

As for the compounds used in the aforementioned preparation methods having, for example, amino group, hydroxyl group, carboxyl group or the like, these groups can be protected with usual protective groups beforehand, and after the reactions, the protective groups can be eliminated by a per se known method.

The compounds obtained by the aforementioned preparation methods can be derived into other compounds by a per se known reaction such as condensation, addition, oxidation, reduction, rearrangement, substitution, halogenation, dehydration, hydrolysis, or an appropriate combination of these.

The salt of the compound A of the present invention may be anhydride, hydrate, or solvate. When only the term "salt" is used in the present invention, the salt may be in the form of anhydride, hydrate, or solvate.

The "anhydride" used in the present invention means a substance in the form of neither hydrate nor solvate, unless especially indicated. The anhydride may also be referred to as "anhydrate".

The number of water molecule contained in hydrate is not particularly limited, and the hydrate may be monohydrate, dihydrate, or the like.

Examples of carboxylate of the compound A include, for example, formate, acetate, lactate, benzoate, citrate, oxalate, fumarate, maleate, succinate, malate, tartrate, aspartate, trichloroacetate, trifluoroacetate, and pamoate of the compound A. Acetate, lactate, benzoate, citrate, oxalate, fumarate, maleate, succinate, malate, tartrate, and pamoate of the compound A are preferred, fumarate, succinate, and pamoate of the compound A are more preferred, fumarate and succinate of the compound A are further preferred, and succinate of the compound A is most preferred.

Examples of mineral acid salt of the compound A include, for example, hydrochloride, hydrobromide hydroiodide, nitrate, phosphate, and sulfate of the compound A. Hydrochloride, hydrobromide, nitrate, phosphate, and sulfate of the compound A are preferred, and hydrochloride and hydrobromide of the compound A are more preferred.

Examples of sulfonate of the compound A include, for example, methanesulfonate, benzenesulfonate, p-toluenesulfonate, mesitylenesulfonate, and naphthalenesulfonate, and benzenesulfonate is preferred.

The salt of the compound A or a crystal thereof of the present invention is preferably a carboxylate of the compound A or a crystal thereof in view of storage stability, and succinate or fumarate of the compound A, and crystals thereof are more preferred.

The crystal of the salt of the compound A of the present invention is characterized by the diffraction peaks observed in powder X-ray diffractometry.

A preferred example of the crystal of the salt of the compound A of the present invention is a crystal of succinate of the compound A showing diffraction peaks at diffraction angles (2θ) of 10.5, 17.1, 19.1, and 22.4° in powder X-ray diffractometry (henceforth also referred to as α-form crystal).

Another preferred example is a crystal of succinate of the compound A showing diffraction peaks at diffraction angles (2θ) of 12.8, 16.1, 21.4, and 28.0° in powder X-ray diffractometry (henceforth also referred to as β-form crystal).

Still another preferred example is a crystal of fumarate of the compound A showing diffraction peaks at diffraction angles (2θ) of 8.6, 13.7, 17.8, and 23.0° in powder X-ray diffractometry.

The crystal of the salt of the compound A of the present invention is also characterized by the absorption peaks observed in an infrared absorption spectrum thereof (ATR method).

A preferred example of the crystal of the salt of the compound A of the present invention is an α-form crystal of succinate of the compound A showing absorption peaks at the wave numbers of 2937, 2218, 1441, 1304 and 1242 cm$^{-1}$ in an infrared absorption spectrum thereof (ATR method).

Another preferred example is a β-form crystal of succinate of the compound A showing absorption peaks at the wave numbers of 2219, 1660, 1512, 1239 and 1121 cm$^{-1}$ in an infrared absorption spectrum thereof (ATR method).

Still another preferred example is a crystal of fumarate of the compound A showing absorption peaks at the wave numbers of 2220, 1594, 1517, 1428 and 1080 cm$^{-1}$ in an infrared absorption spectrum thereof (ATR method).

Diffraction angles (2θ) determined in powder X-ray diffractometry generally contain errors within the range of ±0.2°. Therefore, an expression "diffraction angle (2θ) of X°" used in the present invention means a "diffraction angle (2θ) of (X−0.2) to (X+0.2)°", unless especially indicated. Therefore, not only crystals showing diffraction angles completely agreeing with the diffraction angles defined above in powder X-ray diffractometry, but also crystals showing diffraction angles agreeing with the diffraction angles defined above within such an error range of ±0.2° also fall within the scope of the present invention.

Values of wave number ($cm^{-1}$) determined in infrared absorption spectra (ATR method) generally contain errors within the range of ±2 $cm^{-1}$. Therefore, an expression "wave number Y" used in the present invention means a "wave number of (Y−2) to (Y+2) $cm^{-1}$", unless especially indicated. Therefore, not only crystals showing wave numbers of absorption peaks completely agreeing with the wave numbers of absorption peaks defined above in infrared absorption spectra thereof, but also crystals showing wave numbers of absorption peaks agreeing with the diffraction angles defined above within such an error range of ±2 $cm^{-1}$ also fall within the scope of the present invention.

The salt of the compound A or a crystal thereof of the present invention has superior FLT3 inhibitory activity, shows superior storage stability and/or solubility, and so forth, and thus is useful as an active ingredient of drugs, and useful for a treatment of a disease or condition relating to FLT3. Specifically, the salt of the compound A or a crystal thereof of the present invention is useful for a treatment of ALL, AML, APL, CLL, CML, CNL, AUL, ALCL, PML, JMML, ATL, MDS, or MPD, preferably a treatment of AML or APL, more preferably a treatment of AML.

A pharmaceutical composition containing the salt of the compound A or a crystal thereof of the present invention may usually contain additives used for preparation of pharmaceutical compositions such as excipients, binders, lubricants, disintegrating agents, colorants, corrigents, emulsifiers, surfactants, dissolving aids, suspending agents, isotonic agents, buffering agents, preservatives, anti-oxidants, stabilizers, and absorption enhancers.

The pharmaceutical composition of the present invention means a pharmaceutical composition prepared by using the salt of the compound A or a crystal thereof of the present invention.

The pharmaceutical composition containing the salt of the compound A or a crystal thereof of the present invention may contain only a single kind or two or more kinds of the salts of the compound A or crystals thereof of the present invention among various kinds of salts of the compound A or crystals thereof of the present invention.

As for the administration route of the pharmaceutical composition of the present invention, examples of the administration method include, for example, intravenous, intraarterial, intrarectal, intraperitoneal, intramuscular, intratumoral and intracystic injections, oral administration, dermal administration, use of suppository, and so forth. As for dose and administration frequency, for example, 0.01 to 1000 mg/kg per day of the salt of the present invention can be administered orally or parenterally (by, for example, injection, drip infusion, administration to rectal part, or the like) to an adult once a day, or several times a day with dividing the foregoing dose. Examples of the dosage form of the pharmaceutical composition include tablet, capsule, powder, syrup, granule, pill, suspension, emulsion, solution, powdery preparation, suppository, eye drop, nose drop, ear drop, patch, ointment, and injection.

EXAMPLES

Hereafter, the present invention will be explained with reference to examples. However, the present invention is not limited to these examples. Percent (%) means mass %, unless especially indicated.

An automatic purification system, ISOLERA (produced by Biotage), was used for the purification by column chromatography.

SNAP KP-Sil Cartridge (produced by Biotage) was used as the carrier for silica gel column chromatography, and SNAP KP-NH Cartridge (produced by Biotage) was used as the carrier for basic silica gel column chromatography.

The $^1$H-NMR spectra were measured by using tetramethylsilane as an internal standard, and Bruker AV300 (produced by Bruker), and all the δ values are indicated in terms of ppm.

The MS spectra were measured by using ACQUITY SQD LC/MS System (Waters).

The infrared absorption spectra were measured by using Spectrum 100S (PerkinElmer) according to the descriptions of the Japanese Pharmacopoeia, General Test Procedures, Attenuated Total Reflection Fourier Transform Infrared Spectrometry Method (ATR method).

The powder X-ray diffraction spectra were measured by using RINT-2000 (Rigaku International) under the following conditions.

(Measurement Conditions)

X-ray used: CuKα

Tube voltage: 55 kV

Tube current: 280 mA

Scanning axis: 2θ

The moisture content was measured with Karl-Fischer Aquameter MKC-610 (Kyoto Electronics Manufacturing).

The purities are represented in terms of area % measured by high performance liquid chromatography (HPLC). The HPLC measurement was performed by using Prominence (Shimadzu) under the following conditions.

(Measurement Conditions)

Measurement wavelength: 220 nm

Column: CAPCELL PAK C18 MGII (internal diameter 4.6 mm×length 250 mm)

Column temperature, 40° C.

Flow rate: 1.0 mL/minute

Mobile phase A: 22 mmol/L aqueous phosphoric acid

Mobile phase B: 22 mmol/L phosphoric acid solution in acetonitrile/water=90/10 Gradient cycle: 0.0 min (Solution A/Solution B=80/20), 20.0 min (Solution A/Solution B=60/40), 50.0 min (Solution A/Solution B=0/100), 60.0 min (Solution A/Solution B=0/100), 60.1 min (Solution A/Solution B=80/20), 75.0 min (Solution A/Solution B=80/20)

Preparation Example (1)

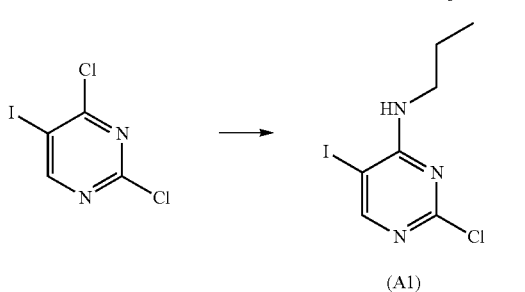

To a solution of 2,4-dichloro-5-iodopyrimidine (5.77 g) synthesized according to the method described in WO2008/155140A1 and N,N-diisopropylethylamine (7.86 mL) in tetrahydrofuran (83 mL), propylamine (3.55 mL) was added under ice cooling, and the mixture was stirred at room temperature for 1 hour. Water and ethyl acetate were added to the reaction mixture. The organic layer was separated, and the aqueous layer was extracted with ethyl acetate. The organic layer and the extract were combined, washed successively with 1.0 mol/L aqueous hydrochloric acid, water, saturated aqueous sodium hydrogencarbonate, and saturated aqueous sodium chloride, and dried over anhydrous magnesium sulfate. The solvent was evaporated under reduced pressure to obtain 2-chloro-5-iodo-N-propylpyrimidin-4-amine (A1, 6.44 g) as oil.

MS m/z (M+H): 298.3

(2)

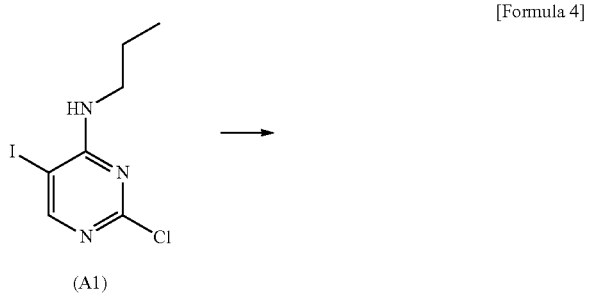

To a solution of 2-chloro-5-iodo-N-propylpyrimidin-4-amine (A1, 9.12 g) in N-methylpyrrolidone (120 mL), 4-aminobenzonitrile (18.1 g) and (1S)-(+)-10-camphorsulfonic acid (35.6 g) were added at room temperature, and the mixture was stirred at 50° C. for 9 hours. The reaction mixture was cooled to room temperature, and then poured into saturated aqueous sodium hydrogencarbonate. The solid was collected by filtration, washed with water, then recrystallized from acetonitrile, and dried under reduced pressure to obtain $N^2$-(4-cyanophenyl)-5-iodo-$N^4$-propylpyrimidine-2,4-diamine (A2, 4.64 g) as white solid.

MS m/z (M+H): 380.2
MS m/z (M−H): 378.2
$^1$H-NMR (CDCl$_3$) δ: 8.16 (1H, s), 7.73 (2H, d, J=8.7 Hz), 7.57 (2H, d, J=8.7 Hz), 7.21 (1H, brs), 5.34 (1H, brs), 3.50-3.42 (2H, m), 1.77-1.64 (2H, m), 1.02 (3H, t, J=7.6 Hz)

(3)

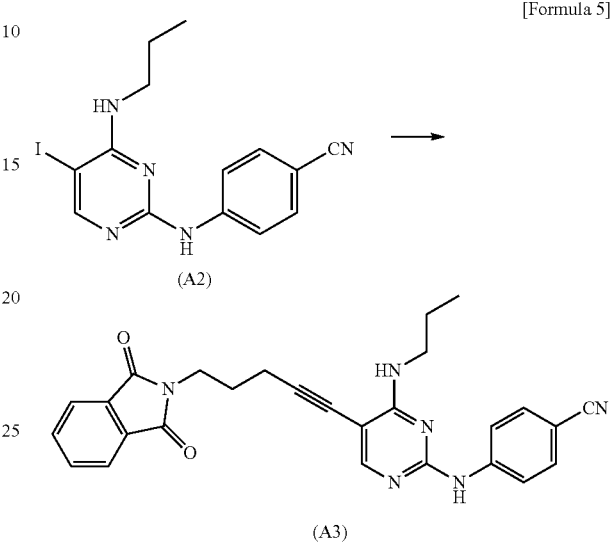

To a solution of $N^2$-(4-cyanophenyl)-5-iodo-$N^4$-propylpyrimidine-2,4-diamine (A2, 687 mg) in N,N-dimethylformamide (10 mL), bis(triphenylphosphine)palladium(II) dichloride (127 mg), copper(I) iodide (104 mg), triethylamine (1.0 mL), and N-(4-pentynyl)phthalimide (464 mg) were added at room temperature under a nitrogen atmosphere, and the mixture was stirred at the same temperature for 2 hours. Water was added to the reaction mixture. The solid was collected by filtration, washed with water, and then dried under reduced pressure to obtain 2-(5-(2-((4-cyanophenyl)amino)-4-(propylamino)pyrimidin-5-yl)-4-pentyn-1-yl)isoindoline-1,3-dione (A3, 1.14 g) as yellow solid.

MS m/z (M+H): 465.3

(4)

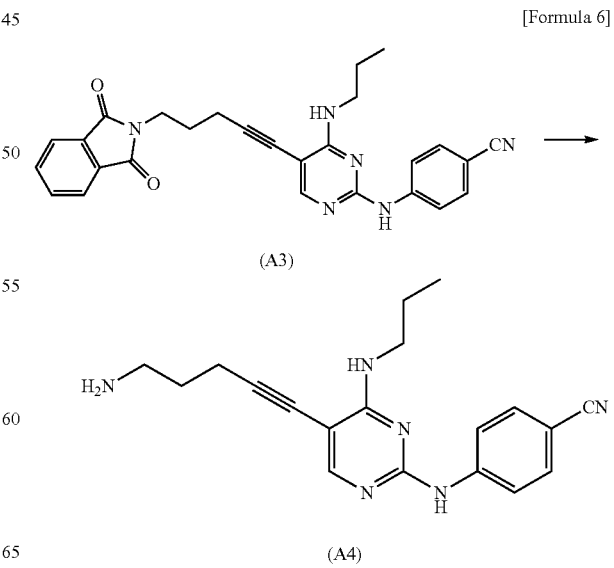

To a solution of 2-(5-(2-((4-cyanophenyl)amino)-4-(propylamino)pyrimidin-5-yl)-4-pentyn-1-yl)isoindoline-1,3-dione (A3, 1.14 g) in tetrahydrofuran (15 mL) and ethanol (15 mL), hydrazine monohydrate (2.0 mL) was added at room temperature, and the mixture was stirred for 45 minutes under reflux by heating. The reaction mixture was cooled to room temperature, and then diluted aqueous hydrochloric acid was added to the reaction mixture until the mixture became acidic. The insoluble matter was removed by filtration, and saturated aqueous sodium hydrogencarbonate was added to the reaction mixture until the mixture became basic. The solid was collected by filtration, washed with water, and then dried under reduced pressure to obtain 5-(5-amino-1-pentyn-1-yl)-$N^2$-(4-cyanophenyl)-$N^4$-propylpyrimidine-2,4-diamine (A4, 459 mg) as white solid.

MS m/z (M+H): 335.3

(5)

(4.80 g) in N,N-dimethylformamide (100 mL), N,N-diisopropylethylamine (8.5 mL) was added at room temperature, and the mixture was stirred at the same temperature for 1 hour and 30 minutes. Saturated aqueous sodium hydrogencarbonate and ethyl acetate were added to the reaction mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 50% hexane/50% ethyl acetate) to obtain (S)-tert-butyl (1-((5-(2-((4-cyanophenyl)amino)-4-(propylamino)pyrimidin-5-yl)-4-pentyn-1-yl)amino)-1-oxopropan-2-yl)(methyl)carbamate (A5, 9.40 g).

MS m/z (M+H): 520.6
MS m/z (M−H): 518.6
$^1$H-NMR (CDCl$_3$) δ: 7.98 (1H, s), 7.76 (2H, d, J=8.6 Hz), 7.57 (2H, d, J=8.6 Hz), 7.30 (1H, brs), 6.41 (1H, brs),

[Formula 7]

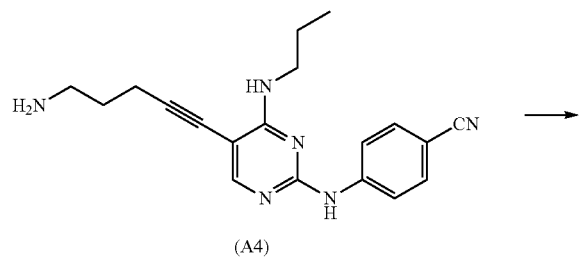

(A4)

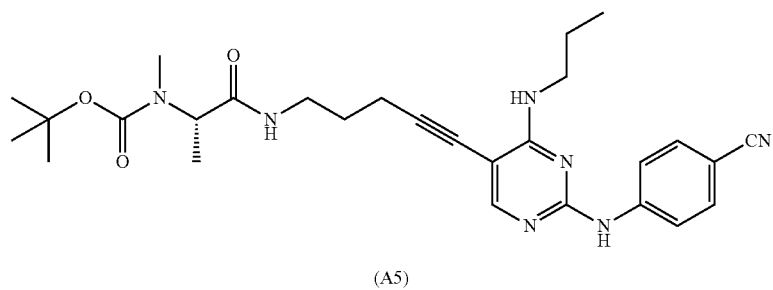

(A5)

To a solution of 5-(5-amino-1-pentyn-1-yl)-$N^2$-(4-cyanophenyl)-$N^4$-propylpyrimidine-2,4-diamine (A4, 7.89 g), N-(tert-butoxycarbonyl)-N-methyl-L-alanine (5.76 g), 1-ethyl-3-(3-dimethylaminopropyl)carbodiimide hydrochloride (6.80 g), and 1-hydroxybenzotriazole monohydrate 6.38-6.08 (1H, brs), 4.72-4.62 (1H, m), 3.58-3.38 (4H, m), 2.80 (3H, s), 2.48 (2H, t, J=6.6 Hz), 1.82-1.68 (4H, m), 1.49 (9H, s), 1.35 (3H, d, J=7.3 Hz), 1.00 (3H, t, J=7.3 Hz)

(6)

[Formula 8]

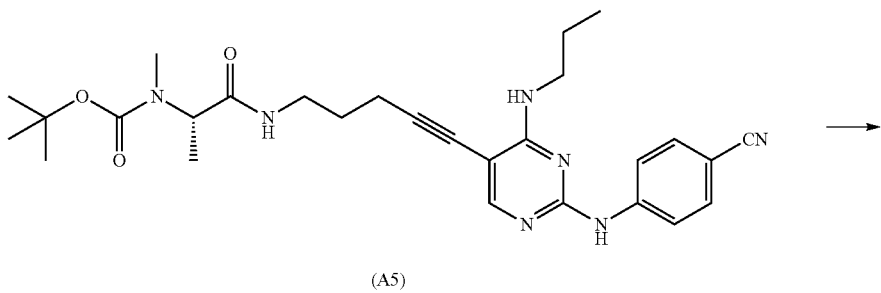

(A5)

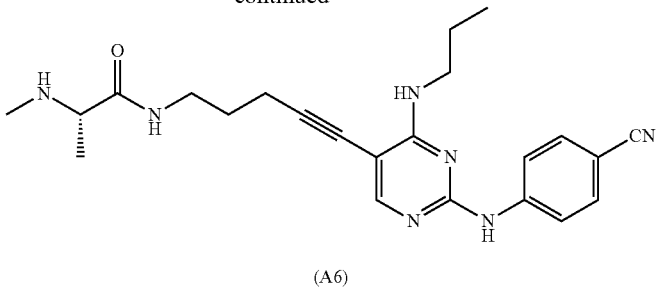

(A6)

To a solution of (S)-tert-butyl (1-((5-(2-((4-cyanophenyl)amino)-4-(propylamino)pyrimidin-5-yl)-4-pentyn-1-yl)amino)-1-oxopropan-2-yl)(methyl)carbamate (A5, 1.26 g) in 1,4-dioxane (10 mL), a 4.0 mol/L solution of hydrochloric acid in 1,4-dioxane (10 mL) was added at room temperature, and the mixture was stirred at the same temperature for 3 hours. The solvent was evaporated under reduced pressure, and ethyl acetate was added to the obtained residue. The solid was collected by filtration, washed with ethyl acetate, and then dried under reduced pressure to obtain (S)—N-(5-(2-((4-cyanophenyl)amino)-4-(propylamino)pyrimidin-5-yl)-4-pentyn-1-yl)-2-(methylamino)propanamide (A6) dihydrochloride (1.12 g) as white solid.

MS m/z (M+H): 420.4
MS m/z (M−H): 418.4

(7)

the reaction mixture, and the solvent was evaporated under reduced pressure. Water and ethyl acetate were added to the obtained residue. The organic layer was separated, and the aqueous layer was extracted with ethyl acetate. The organic layer and the extract were combined, and dried over anhydrous sodium sulfate, and the solvent was evaporated under reduced pressure. Acetonitrile was added to the obtained residue, and the solid was collected by filtration and purified by basic silica gel column chromatography (eluent, 95% ethyl acetate/5% methanol) to obtain (S,E)-N-(1-(5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-enamide (compound A, 12.5 g).

MS m/z (M+H): 531.5
MS m/z (M−H): 529.5

[Formula 9]

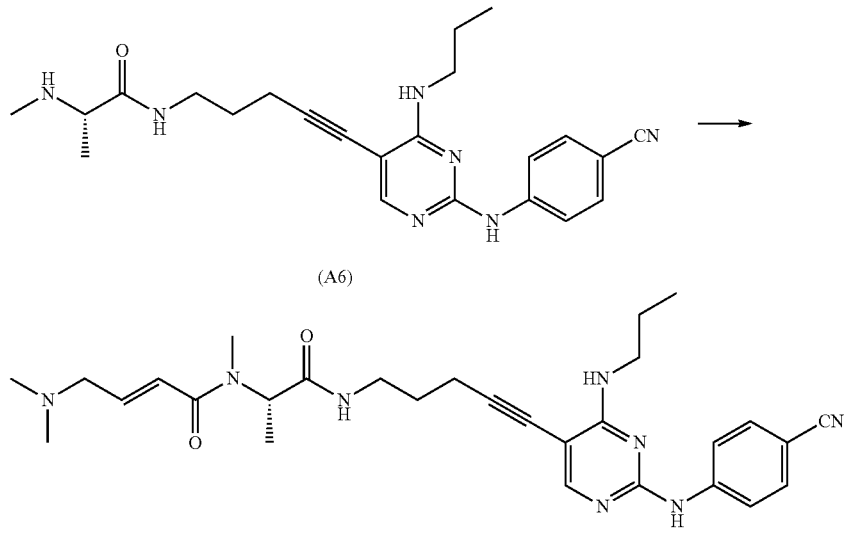

To a solution of (S)—N-(5-(2-((4-cyanophenyl)amino)-4-(propylamino)pyrimidin-5-yl-4-pentyn-1-yl-2-(methylamino)propanamide (A6) dihydrochloride (19.0 g) and 4-dimethylaminocrotonic acid hydrochloride (22.3 g) in N,N-dimethylformamide (550 mL), N-methylmorpholine (42.4 mL) was added at room temperature, and the mixture was stirred at the same temperature for 10 minutes. Then, isobutyl chloroformate (15.2 mL) was added dropwise to the mixture under ice cooling, and the mixture was stirred at the same temperature for 1 hour and 30 minutes. Saturated aqueous sodium hydrogencarbonate (200 mL) was added to $^1$H-NMR (CDCl$_3$) δ: 8.05 (1H, s), 7.97 (1H, s), 7.79 (2H, d, J=8.6 Hz), 7.56 (2H, d, J=9.2 Hz), 6.94 (1H, dt, J=15.2, 5.3 Hz), 6.71 (1H, t, J=5.6 Hz), 6.44-6.42 (2H, m), 5.20 (1H, q, J=7.3 Hz), 3.49-3.45 (4H, m), 3.11 (2H, d, J=5.3 Hz), 3.01 (3H, s), 2.45 (2H, t, ÅJ=6.6 Hz), 2.27 (6H, s), 1.77-1.66 (4H, m), 1.36 (3H, d, J=7.3 Hz), 1.00 (3H, t, J=7.3 Hz)

Example 1

To a suspension of the compound A (3.50 g) in acetone (70 mL), succinic acid (779 mg) was added at room temperature, and dissolution was visually confirmed under reflux by heating. The reaction mixture was gradually cooled to room temperature, and left standing for one day. The solid was collected by filtration, washed with acetone, and then dried under reduced pressure to obtain white solid (4.08 g).

A suspension of the obtained white solid (1.20 g) in acetonitrile (24 mL) was refluxed by heating, and dissolution was visually confirmed. This solution was gradually cooled to room temperature, and left standing for 3 days. The solid was collected by filtration, washed with acetonitrile, and then dried under reduced pressure to obtain α-form crystals of succinate of the compound A (1.02 g).

Moisture content: 0.50% (weight ratio)

$^1$H-NMR (DMSO-D$_6$) δ: 9.79 (1H, s), 8.00-7.88 (4H, m), 7.68 (2H, d, J=8.6 Hz), 7.20-7.10 (1H, m), 6.68-6.50 (2H, m), 5.01 (1H, q, J=7.0 Hz), 3.40 (2H, dt, J=6.8, 6.8 Hz), 3.32-3.20 (2H, m), 3.12 (2H, d, J=5.3 Hz), 2.95 (3H, s), 2.47-2.38 (6H, m), 2.21 (6H, s), 1.72-1.54 (4H, m), 1.34-1.24 (3H, m), 0.91 (3H, t, J=7.3 Hz)

Figure 2:
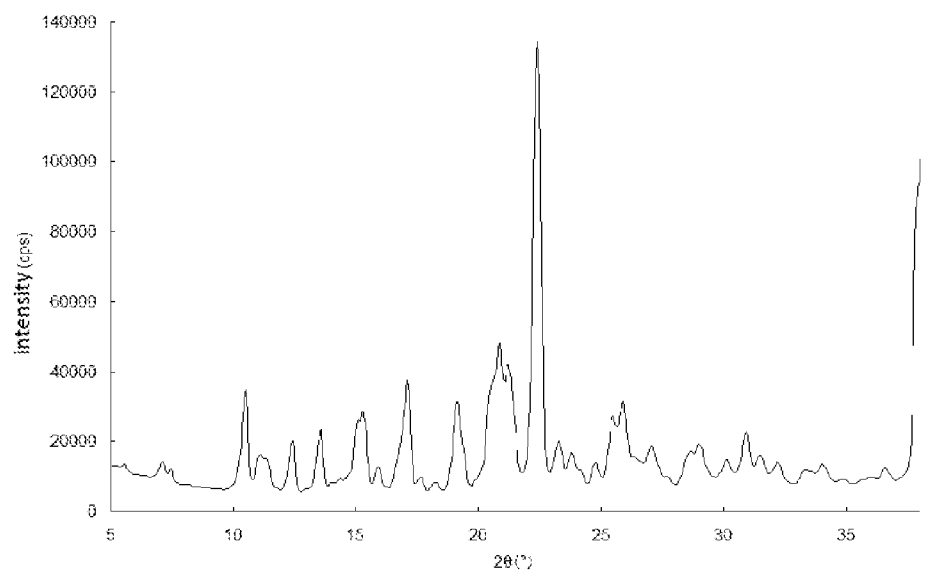
FIG. 2 shows an example of powder X-ray diffraction pattern of α-form crystal of succinate of the compound A.

The infrared absorption spectrum (ATR method) of the obtained α-form crystal of succinate of the compound A is shown in FIG. 1 and Table 1, and the powder X-ray diffraction pattern of the same is shown in FIG. 2 and Table 2.

TABLE 1

| Wave number (cm$^{-1}$) |
| --- |
| 2937 |
| 2218 |
| 1441 |
| 1304 |
| 1242 |

TABLE 2

| 2 θ | d(Å) |
| --- | --- |
| 10.5 | 8.425 |
| 13.6 | 6.511 |
| 15.3 | 5.791 |
| 17.1 | 5.185 |
| 19.1 | 4.647 |
| 20.9 | 4.250 |
| 22.4 | 3.969 |
| 25.5 | 3.493 |
| 25.9 | 3.440 |

Example 2

To a suspension of the compound A (5.50 g) in acetone (110 mL), succinic acid (1.22 g) was added at room temperature, and dissolution was visually confirmed under reflux by heating. The reaction mixture was gradually cooled to room temperature, and left standing for one day. The solid was collected by filtration, washed with acetone, and then dried under reduced pressure to obtain pale yellow solid (6.22 g).

A suspension of the obtained pale yellow solid (150 mg) in 1,4-dioxane (3.0 mL) was refluxed by heating, and dissolution was visually confirmed. This solution was gradually cooled to room temperature, and left standing for 12 days. The solid was collected by filtration, washed with 1,4-dioxane, and then dried under reduced pressure to obtain β-form crystals of succinate of the compound A (141 mg).

$^1$H-NMR (DMSO-D$_6$) δ: 9.79 (1H, s), 8.00-7.88 (4H, m), 7.68 (2H, d, J=8.6 Hz) 7.20-7.10 (1H, m), 6.68-6.50 (2H, m), 5.00 (1H, q, J=6.8 Hz), 3.40 (2H, dt, J=6.8, 6.8 Hz), 3.32-3.20 (2H, m), 3.10 (2H, d, J=5.3 Hz), 2.95 (3H, s), 2.47-2.38 (6H, m), 2.20 (6H, s), 1.72-1.54 (4H, m), 1.34-1.24 (3H, m), 0.91 (3H, t, J=7.3 Hz).

Figure 3:
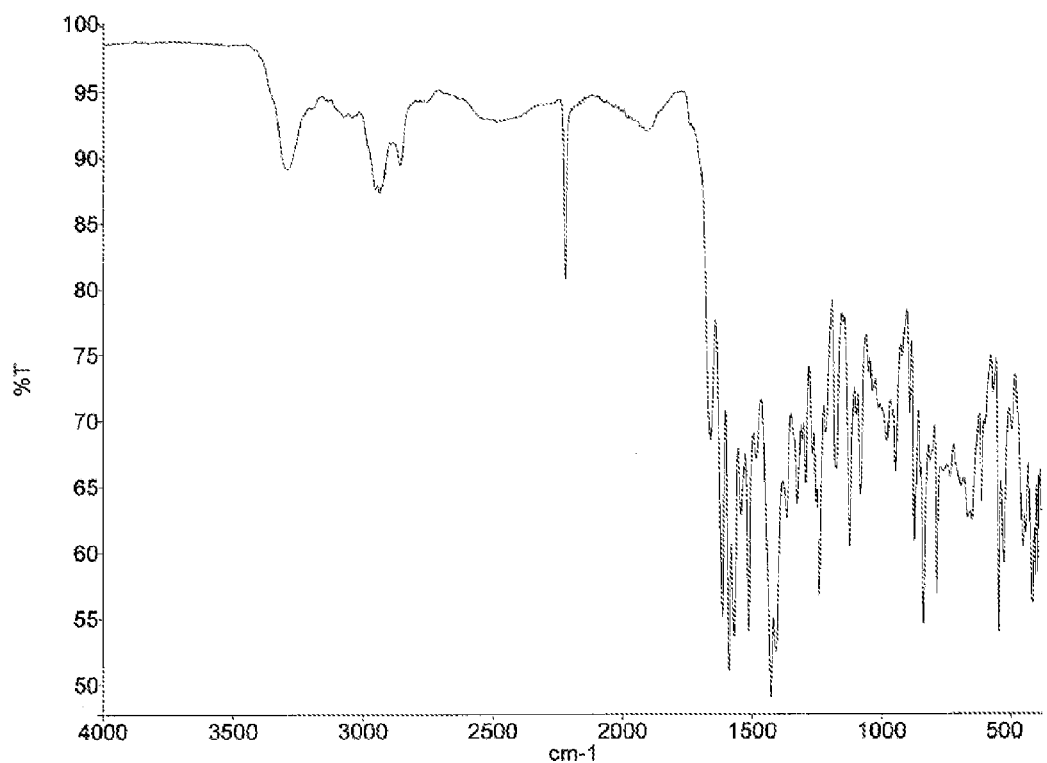
FIG. 3 shows an example of infrared absorption spectrum (ATR method) of β-form crystal of succinate of the compound A.
Figure 4:
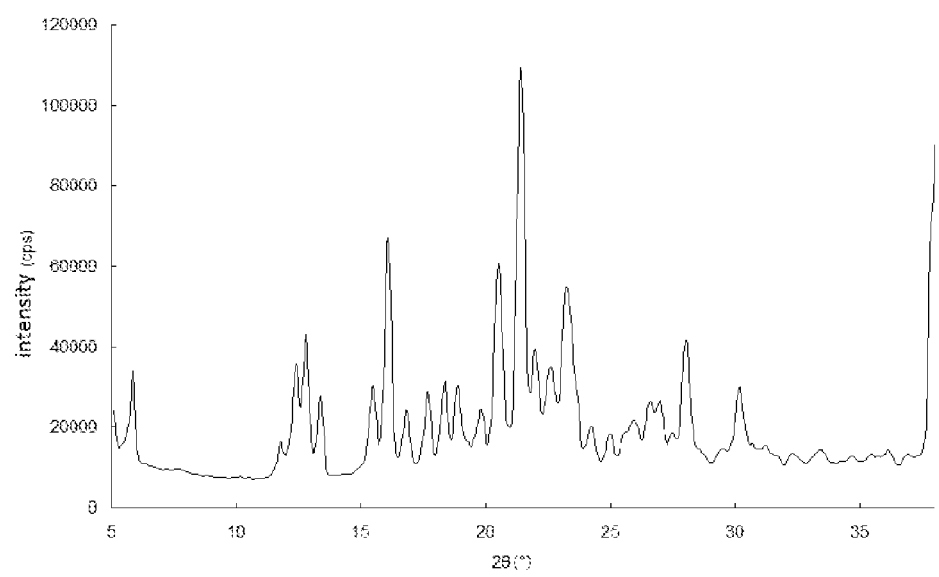
FIG. 4 shows an example of powder X-ray diffraction pattern of β-form crystal of succinate of the compound A.

The infrared absorption spectrum of the obtained β-form crystal of succinate of the compound A is shown in FIG. 3 and Table 3, and the powder X-ray diffraction pattern of the same is shown in FIG. 4 and Table 4.

TABLE 3

| Wave number (cm$^{-1}$) |
| --- |
| 2219 |
| 1660 |
| 1512 |
| 1239 |
| 1121 |

TABLE 4

| 2 θ | d(Å) |
| --- | --- |
| 12.4 | 7.138 |
| 12.8 | 6.916 |
| 15.5 | 5.717 |
| 16.1 | 5.505 |
| 20.5 | 4.332 |
| 21.4 | 4.152 |
| 23.2 | 3.834 |
| 28.0 | 3.187 |

Example 3

To a suspension of the compound A (1.50 g) in ethanol (30 mL), fumaric acid (328 mg) was added at room temperature, the mixture was stirred with heating at 70° C., and dissolution was visually confirmed. The reaction mixture was gradually cooled to room temperature, and left standing for 3 days. The solid was collected by filtration, washed with ethanol, and then dried under reduced pressure to obtain white solid (1.67 g).

The compound A (0.53 g) was added to a suspension of the obtained white solid (1.67 g) in ethanol (30 mL), the mixture was stirred with heating at 80° C., and dissolution was visually confirmed. This solution was gradually cooled to room temperature, and left standing for 6 hours. The solid was collected by filtration, washed with ethanol, and then dried under reduced pressure to obtain fumarate of the compound A (1.96 g) as white solid.

Moisture content: 1.0% (weight ratio)

$^1$H-NMR (DMSO-D$_6$) δ: 9.79 (1H, s), 8.00-7.90 (4H, m), 7.68 (2H, d, J=8.6 Hz) 7.20-7.12 (1H, m), 6.67-6.55 (4H, m), 5.00 (1H, q, J=7.3 Hz), 3.40 (2H, q, J=6.6 Hz), 3.34-3.22 (4H, m), 2.95 (3H, s), 2.44 (2H, t, J=6.6 Hz), 2.24 (6H, s), 1.72-1.56 (4H, m), 1.34-1.24 (3H, m), 0.91 (3H, t, J=7.3 Hz)

Figure 5:
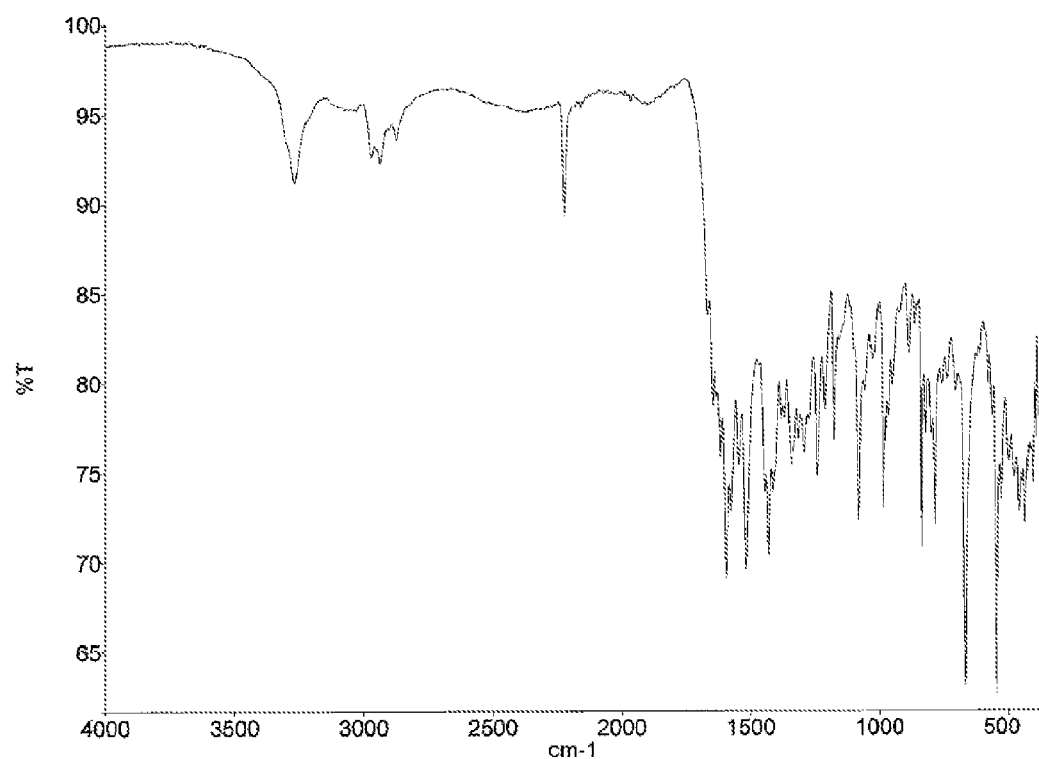
FIG. 5 shows an example of infrared absorption spectrum (ATR method) of crystal of fumarate of the compound A.
Figure 6:
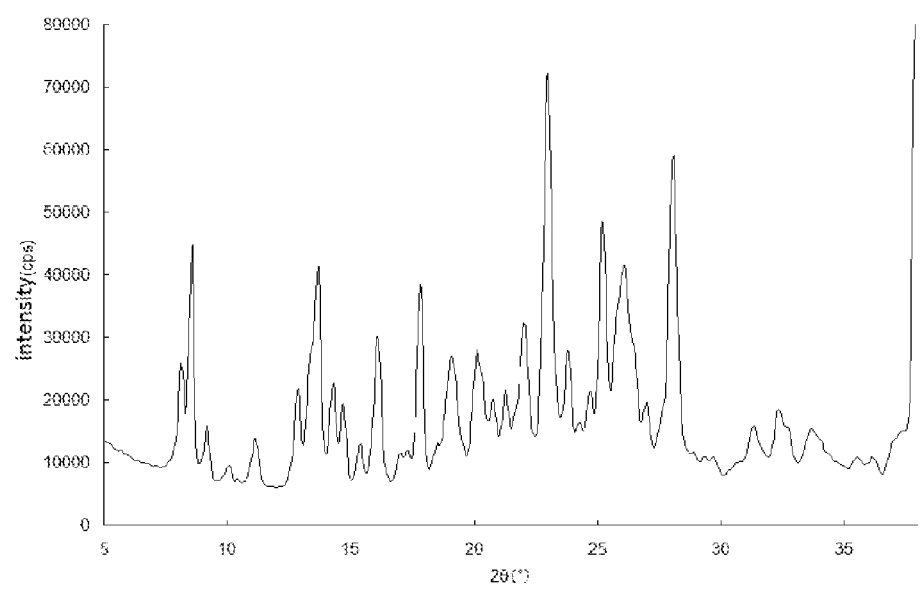
FIG. 6 shows an example of powder X-ray diffraction pattern of crystal of fumarate of the compound A.

The infrared absorption spectrum of the obtained fumarate of the compound A is shown in FIG. 5 and Table 5, and the powder X-ray diffraction pattern of the same is shown in FIG. 6 and Table 6.

TABLE 5

| Wave number (cm$^{-1}$) |
| --- |
| 2220 |
| 1594 |
| 1517 |

TABLE 5-continued

| Wave number (cm$^{-1}$) |
| --- |
| 1428 |
| 1080 |

TABLE 6

| 2 θ | d(Å) |
| --- | --- |
| 8.6 | 10.282 |
| 12.9 | 6.862 |
| 13.7 | 6.464 |
| 16.1 | 5.505 |
| 17.8 | 4.983 |
| 20.1 | 4.418 |
| 23.0 | 3.867 |
| 25.2 | 3.534 |
| 28.1 | 3.176 |

Example 4

To a suspension of pamoic acid (73 mg) in water, 3.0 mol/L aqueous sodium hydroxide (126 μL) was added at room temperature (solution 1). A suspension of the compound A (100 mg) in acetone (10 mL) was stirred with heating at 60° C., and dissolution was visually confirmed (solution 2). The solution 2 was added to the solution 1 at room temperature, then acetic acid (22 μL), acetone, and water were added to the mixture, and the mixture was stirred for 30 minutes. The solid was collected by filtration, washed with water, and then dried under reduced pressure to obtain pamoate of the compound A (132 mg) as pale yellow solid.

$^1$H-NMR (DMSO-D$_6$) δ: 9.79 (1H, s), 8.32 (2H, s), 8.16 (2H, d, J=8.6 Hz), 8.00-7.94 (4H, m), 7.76 (2H, d, J=7.3 Hz), 7.68 (2H, d, J=8.6 Hz), 7.25 (2H, t, J=7.3 Hz), 7.18-7.06 (3H, m), 6.86 (1H, d, J=15.2 Hz), 6.68-6.54 (1H, m), 4.99 (1H, q, J=7.3 Hz), 4.74 (2H, s), 3.92-3.82 (2H, m), 3.60-3.20 (4H, m), 2.98 (3H, s), 2.77 (6H, s), 2.44 (2H, t, J=6.6 Hz), 1.72-1.54 (4H, m), 1.36-1.25 (3H, m), 0.91 (3H, t, J=7.6 Hz)

Example 5

A suspension of the compound A (150 mg) in acetone (4.5 mL) was refluxed by heating, and dissolution was visually confirmed. This solution was gradually cooled to 40° C., a 4.0 mol/L solution of hydrochloric acid in 1,4-dioxane (141 μL) was added to the solution, and the mixture was left standing for 5 days. The solid was collected by filtration, washed with acetone, and then dried under reduced pressure to obtain hydrochloride of the compound A (112 mg) as white solid.

$^1$H-NMR (DMSO-D$_6$) δ: 8.73-8.65 (1H, m), 8.17 (1H, s), 8.15-8.10 (1H, m), 7.87-7.84 (4H, m), 7.86-7.83 (1H, m), 7.09-6.88 (1H, m), 6.75-6.58 (1H, m), 4.99 (1H, q, J=7.3 Hz), 3.93-3.86 (2H, m), 3.49-3.42 (2H, m), 3.28-3.22 (2H, m), 3.00 (3H, s), 2.75-2.72 (6H, m), 2.48 (2H, t, J=6.6 Hz), 1.73-1.59 (4H, m), 1.37-1.28 (3H, m), 0.92 (3H, t, J=7.3 Hz)

Example 6

A suspension of the compound A (1.00 g) in ethanol (20 mL) was stirred with heating at 70° C., and dissolution was visually confirmed. Phosphoric acid (238 μL) was added to this solution, and the mixture was gradually cooled to room temperature, and left standing for 3 hours and 30 minutes. The solid was collected by filtration, washed twice with ethanol, and then dried under reduced pressure to obtain phosphate of the compound A (0.75 g) as pale yellow solid.

$^1$H-NMR (DMSO-D$_6$) δ: 9.84 (1H, s), 8.02-7.95 (3H, m), 7.69 (2H, d, J=9.2 Hz), 7.22-7.13 (1H, m), 6.89-6.77 (1H, m), 6.71-6.55 (2H, m), 5.02 (1H, q, J=6.6 Hz), 3.74-3.62 (2H, m), 3.51-3.35 (2H, m), 3.49-3.20 (2H, m), 2.99 (3H, s), 2.61 (6H, s), 2.45 (2H, t, J=6.3 Hz), 1.75-1.57 (4H, m), 1.37-1.27 (3H, m), 0.92 (3H, t, J=7.6 Hz)

Example 7

A suspension of the compound A (1.00 g) in ethanol (20 mL) was stirred with heating at 70° C., and dissolution was visually confirmed. Sulfuric acid (211 μL) was added to this solution, and the mixture was gradually cooled to room temperature, and left standing for 3 hours. The solid was collected by filtration, washed twice with ethanol, and then dried under reduced pressure to obtain sulfate of the compound A (1.10 g) as white solid.

$^1$H-NMR (DMSO-D$_6$) δ: 9.67 (1H, s), 8.36-8.27 (1H, m), 8.11-8.07 (1H, m), 8.04-7.98 (1H, m), 7.88-7.80 (4H, m), 6.95-6.85 (1H, m), 6.66-6.50 (1H, m), 4.99 (1H, q, J=7.0 Hz), 3.96-3.88 (2H, m), 3.47-3.39 (2H, m), 3.30-3.22 (2H, m), 2.99 (3H, s), 2.80 (6H, s), 2.48 (2H, t, J=6.6 Hz), 1.74-1.56 (4H, m), 1.37-1.27 (3H, m), 0.91 (3H, t, J=7.6 Hz)

Example 8

Benzenesulfonic acid monohydrate (132 mg) was added to a suspension of the compound A (200 mg) in water (5 mL) at room temperature, the mixture was stirred with heating at 50° C., and dissolution was visually confirmed. The reaction mixture was cooled to room temperature, and then the solvent was evaporated under reduced pressure to obtain benzenesulfonate of the compound A as oil.

Example 9

A suspension of the compound A (150 mg) in acetone (4.5 mL) was refluxed by heating, and dissolution was visually confirmed. Hydrobromic acid (64 μL) was added to this solution, and the mixture was gradually cooled to room temperature. The solid was collected by filtration, washed with acetone, and then dried under reduced pressure to obtain hydrobromide of the compound A (98 mg) as pale yellow solid.

Hereafter, usefulness of the compounds of the present invention will be explained with reference to the following test examples.

Test Example 1

FLT3 Inhibition Test

For the FLT3 enzyme inhibition test, glutathione S-transferase (GST)-fused human FLT3 protein (intracellular region, 564 to 993 as, Carna Biosciences) produced by using a baculovirus expression system was used.

A reaction mixture (9 μL) containing the FLT3 protein and a test compound of a predetermined concentration (1.2 μg of FLT3, 100 mM HEPES, 10 mM MgCl$_2$, 25 mM NaCl, 0.01% BSA, 1 mM DTT, pH 7.5) was left standing at 25° C. for 15 minutes. Then, 3 μL (final concentration, 0.25 μM) of a substrate peptide, biotin-AAA-AEEEEYFELVAKKK (Toray Industries), and 3 μL (final concentration, 50 μM) of ATP (Sigma-Aldrich) were added to the reaction mixture, and the mixture was shaken for 2 minutes, and then left standing at 25° C. for 30 minutes to allow the enzymatic reaction.

Then, 30 μL of an enzymatic reaction termination solution containing Streptavidin-Xlent (Cisbio) and Mab PT66-K (Cisbio) (5 μg/mL streptavidin, 0.19 μg/mL PT66-K, 30 mM HEPES (pH 7.0), 150 mM KF, 75 mM EDTA, 0.15% BSA, 0.075% Tween 20) was added to the reaction mixture to terminate the enzymatic reaction, and the reaction mixture was left standing at room temperature for 1 hour to allow the antigen-antibody reaction. Then, phosphorylation of the substrate peptide was measured by measuring time decomposition fluorescence (615 nm and 665 nm) using Envision (PerkinElmer).

The results are shown in Table 7.

Test Example 2

Leukemic Cell Growth Inhibition Test

A leukemic cell growth inhibition test was performed by using the leukemic cell strains MV4-11 (ATCC Number, CRL-9591) and MOLM-13 (DSMZ Number, ACC554).

The leukemic cell growth inhibition test was performed by the method described below.

For the purpose of measuring growth inhibition with a test compound, the total cell count was quantified on the basis of the total cellular ATP concentration using the CellTitet-Glo (PerkinElmer) reagent that enables quantification of ATP concentration based on the luciferin-luciferase reaction. The MOLM-13 or MV4-11 cells were added to the RPMI medium containing penicillin (100 units/mL), streptomycin (100 μg/mL), and 10% FBS at a density of $2 \times 10^5$ cells/ml, and 50 μL (10,000 cells) of the mixture was inoculated to each well of a 96-well plate (Corning).

A serially diluted solution of a test compound or 0.1% DMSO (solvent control) in a volume of 50 μL was added to the cells, and then the cells were cultured for 72 hours under the standard cell proliferation conditions (37° C., 5% $CO_2$) to allow proliferation of the cells. In order to measure the total cell proliferation, equal volume of the CellTitet-Glo reaction mixture was added to each well in accordance with the instructions attached to CellTitet-Glo, and luminescence count was quantified (relative light unit, RLU).

The RLU signal observed for the DMSO solvent control after 72 hours of culture was defined as a signal indicating 0% inhibition, and the $GI_{50}$ value for the growth inhibition corresponds to a concentration of a compound that provides 50% inhibition of the total cell proliferation observed in the DMSO solvent control. Each data point was obtained from samples prepared in duplicate. The $GI_{50}$ values were calculated by the non-linear regression fitting (Fit Model (205)) according to a sigmoid dose-reaction equation using the XLfit software.

The results are shown in Table 7.

TABLE 7

| | FLT3 enzyme inhibition test $IC_{50}$ (nmol/L) | MV4-11 cell growth inhibition test $GI_{50}$ (nmol/L) | MOLM-13 cell growth inhibition test $GI_{50}$ (nmol/L) |
|---|---|---|---|
| Example 1 | 0.18 | 0.52 | 1.47 |
| Example 2 | 0.22 | 0.60 | 1.50 |
| Example 3 | 0.21 | 0.60 | 1.60 |

The salts of the compound A of the present invention showed outstanding FLT3 enzyme-inhibitory activities and leukemic cell growth inhibitory activities.

Test Example 3

Solubility Test

The compounds of Examples 1 and 3 were chosen as test compounds.

The compound A was chosen as a comparative compound.

The test compounds and the comparative compound were each added to water, and each mixture was stirred at room temperature for 24 hours. The insoluble matter was removed by filtration using a membrane filter (0.2 μm). The filtrate was analyzed by HPLC to obtain solubility.

The results are shown in Table 8.

TABLE 8

| Test compound | Solubility (mg/mL) |
|---|---|
| Example 1 | 70.0 |
| Example 3 | 0.89 |
| Compound A | 0.02 |

The salts of the compound A of the present invention showed outstanding solubility.

Test Example 4

Storage Stability Test (1)

Crystals of the compounds of Examples 1 and 3 were chosen as test substances.

Each test substance (200 mg) was put into a glass bottle of an open state, and stored for 2 weeks under the storage condition 1 (25° C., 75% relative humidity), or the storage condition 2 (40° C., 75% relative humidity). Purity and moisture content of the test substance were measured before the start of the test and after the end of the test.

The purities and moisture contents of the test substances measured before the start of the test and after the end of the test are shown in Table 9.

TABLE 9

| Test substance | | Purity (%) | Moisture content (%) |
|---|---|---|---|
| Example 1 | Before start of test | 99.6 | 0.5 |
| | Storage condition 1 | 99.6 | 0.2 |
| | Storage condition 2 | 99.6 | 0.2 |
| Example 2 | Before start of test | 99.7 | 1.7 |
| | Storage condition 1 | 99.6 | 3.2 |
| | Storage condition 2 | 99.6 | 2.1 |

The salts of the compound A of the present invention showed outstanding storage stability.

The crystals obtained in Examples 1 and 3 showed little change of the purity and moisture content even after the storage over 2 weeks, and thus showed superior storage stability.

Test Example 4

Storage Stability Test (2)

The crystals of the compound of Example 1 were chosen as test substance.

The test substance (200 mg) was put into double plastic bag, and the opening was tied up. The bag was stored for 4 weeks under the storage condition 1 (25° C., 75% relative humidity), or the storage condition 2 (40° C., 75% relative humidity). Purity and moisture content of the test substance were measured before the start of the test and after the end of the test.

The purities and moisture contents of the test substance measured before the start of the test and after the end of the test are shown in Table 10.

TABLE 10

| Test substance | | Purity (%) | Moisture content (%) |
|---|---|---|---|
| Example 1 | Before start of test | 99.4 | 0.2 |
| | Storage condition 1 | 99.4 | 0.2 |
| | Storage condition 2 | 99.4 | 0.2 |

The salt of the compound A of the present invention showed outstanding storage stability.

INDUSTRIAL APPLICABILITY

The salt of the compound A or a crystal thereof of the present invention has outstanding FLT3 inhibitory activity and superior physicochemical properties as drugs, such as storage stability and solubility. Therefore, it is useful for treatment of a disease or condition relating to FLT3.

The invention claimed is:

1. A crystal of succinate of (S,E)-N-(1-((5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-enamide, which shows diffraction peaks at diffraction angles (2θ) of 10.5, 17.1, 19.1, and 22.4° in powder X-ray diffractometry, or
    a crystal of succinate of (S,E)-N-(1-((5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-enamide, which shows diffraction peaks at diffraction angles (2θ) of 12.8, 16.1, 21.4, and 28.0° in powder X-ray diffractometry, or
    a crystal of fumarate of (S,E)-N-(1-((5-(2-((4-cyanophenyl)amino)-4-(propylamino)pyrimidin-5-yl)pent-4-yn-1-yl)amino)-1-oxopropan-2-yl)-4-(dimethylamino)-N-methylbut-2-enamide, which shows diffraction peaks at diffraction angles (2θ) of 8.6, 13.7, 17.8, and 23.0° in powder X-ray diffractometry.

2. A pharmaceutical composition containing the crystal according to claim 1.

* * * * *